(12) United States Patent
Hui et al.

(10) Patent No.: US 7,294,649 B2
(45) Date of Patent: Nov. 13, 2007

(54) METHAMPHETAMINE DERIVATIVES AND CONJUGATES FOR IMMUNOASSAY

(75) Inventors: Raymond A. Hui, Indianapolis, IN (US); Stephen S. Vitone, Indianapolis, IN (US)

(73) Assignee: Roche Diagnostics Operatins, Inc., Indianapolis, IN (US)

( * ) Notice: Subject to any disclaimer, the term of this patent is extended or adjusted under 35 U.S.C. 154(b) by 363 days.

(21) Appl. No.: 11/016,619

(22) Filed: Dec. 17, 2004

(65) Prior Publication Data

US 2006/0134711 A1  Jun. 22, 2006

(51) Int. Cl.
- *A61K 31/4015* (2006.01)
- *A61K 31/135* (2006.01)
- *C07D 207/40* (2006.01)
- *C07D 233/30* (2006.01)

(52) U.S. Cl. .................. 514/425; 514/649; 564/163; 548/545

(58) Field of Classification Search ........... 548/545; 564/163, 336; 514/425, 649
See application file for complete search history.

(56) References Cited

U.S. PATENT DOCUMENTS

| 4,041,076 A | 8/1977 | Avenia et al. |
|---|---|---|
| 5,135,863 A * | 8/1992 | Hu et al. .................. 435/188 |
| 5,328,828 A | 7/1994 | Hu et al. |
| 5,501,987 A | 3/1996 | Ordonez et al. |
| 2001/0051158 A1 | 12/2001 | Owens et al. |
| 2003/0119083 A1 | 6/2003 | Owens et al. |
| 2003/0170917 A1 | 9/2003 | Hui et al. |
| 2004/0077021 A1 | 4/2004 | Hui et al. |

FOREIGN PATENT DOCUMENTS

| EP | 0375422 B1 | 6/1990 |
|---|---|---|
| WO | WO 01/81424 A1 | 11/2001 |

* cited by examiner

*Primary Examiner*—Joseph K. McKane
*Assistant Examiner*—Janet L Coppins
(74) *Attorney, Agent, or Firm*—Marilyn L. Amick; Roche Diagnostics Operations, Inc.

(57) ABSTRACT

Compounds of methamphetamine derivatives having a meta-substituted alkyl linker on the benzene ring and a protective group on the nitrogen of the methamphetamine hapten. Such compounds have the structure

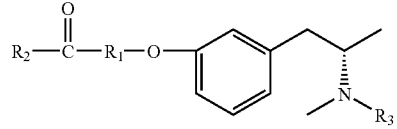

wherein $R_1$ is an alkyl linker comprising 2-15 carbon atoms and 0-6 heteroatoms, $R_2$ is a leaving group, and $R_3$ is a protecting group.

6 Claims, 11 Drawing Sheets

[α]D +15.7° (589nm, C=1, CHCl3).

METHAMPHETAMINE DERIVATIVES AND CONJUGATES FOR IMMUNOASSAY

FIELD OF THE INVENTION

The present invention relates generally to the field of immunoassay methods for determination of drugs of abuse in biological samples, in particular, to immunoassay methods for determination of amphetamine-class drugs, and more particularly, to methamphetamine derivatives and conjugates useful therefor.

BACKGROUND OF THE INVENTION

The use and abuse of a class of illicit designer drugs known commonly as "ecstasy-class drugs" have increased significantly in recent years. These compounds, which are derivatives of amphetamine distinguished by having a fused methylenedioxy phenyl ring system, include MDA (3,4-methylenedioxyamphetamine), MDMA, also known as "Ecstasy" (3,4-methylenedioxy-N-methylamphetamine), MDEA, also known as "Eve" (3,4-methylenedioxy-N-ethylamphetamine), BDB (3,4-methylenedioxyphenyl-2-butanamine), and MBDB (3,4-methylenedioxyphenyl-N-methylbutanamine).

Heretofore, methods for the detection of ecstasy-class drugs have primarily involved immunoassays originally developed for the detection of amphetamine and/or methamphetamine. The detection of an ecstasy-class drug by such assays relies on the limited cross-reactivities that may coincidentally exist between the ecstasy-class drug and the amphetamine and/or methamphetamine antibodies. A positive result obtained by such an assay may still not indicate which particular substance or member of the methylenedioxy (MD) class of derivatives is present in a sample.

In general, amphetamine and methamphetamine immunoassays are relatively insensitive to, and non-specific for, ecstasy-class drugs. Such assays show particularly limited recognition for the MDEA derivative.

The present invention is directed to remedying these and other problems relating to the use of conventional amphetamine and/or methamphetamine immunoassays for the detection of members of the methylenedioxy class, or ecstasy-class, drugs.

In testing for drugs of abuse, immunoassays, particularly competitive binding immunoassays, have proven to be especially advantageous. In competitive binding immunoassays, an analyte in a biological sample competes with a labeled reagent, or analyte analog, or tracer, for a limited number of receptor binding sites on antibodies specific for the analyte and analyte analog. Enzymes such as β-galactosidase and peroxidase, fluorescent molecules such as fluorescein compounds, radioactive compounds such as $^{125}I$, and microparticles are common labeling substances used as tracers. The concentration of analyte in the sample determines the amount of analyte analog which will bind to the antibody. The amount of analyte analog that will bind is inversely proportional to the concentration of analyte in the sample because the analyte and the analyte analog each bind to the antibody in proportion to their respective concentrations. The amount of free or bound analyte analog can then be determined by methods appropriate to the particular label being used.

Currently popular are automated assays based on kinetic interaction of microparticles in a solution as measured by changes in light transmission. In the absence of sample drug, free antibody binds to drug-microparticle conjugates causing the formation of particle aggregates. As the aggregation reaction proceeds in the absence of sample drug, absorbance increases. When a sample contains a drug in question, the drug competes with a particle-bound drug derivative for free antibody. Antibody bound to sample drug is no longer available to promote particle aggregation, and subsequent particle lattice formation is inhibited. The presence of sample drug diminishes increasing absorbance in proportion to concentration of drug in the sample. Sample drug content is determined relative to the value obtained for a known cutoff concentration of drug.

A problem in assays for amphetamine-class drugs is that prior art methods do not provide sufficient cross-reactivity with and displacement from antibodies to measure all the amphetamine-class analytes in a sample, especially amphetamine, methamphetamine, 3,4-methylenedioxyamphetamine (MDA), 3,4-methylenedioxy-N-methylamphetamine (MDMA), and 3,4-methylenedioxy-N-ethylamphetamine (MDEA), with sufficient sensitivity. The methamphetamine derivatives of the present invention overcome such problems by providing the required cross-reactivity with and displacement from methamphetamine antibodies to sensitive measurement of amphetamine, methamphetamine, and ecstasy-class compounds.

Another problem overcome by the present invention is that of unwanted conjugation of haptens through the free amino group on the methamphetamine hapten. The derivatives of the present invention avoid this problem.

In U.S. Pat. No. 5,135,863 issued Aug. 4, 1992, Hu et al. describe conjugates comprising a label bound to an analog of amphetamine or methamphetamine via a thiol linkage. The conjugates further comprise a linker bonded to the benzene ring at the meta- or para-position, and the amphetamine nitrogen is unprotected.

In U.S. patent application Ser. No. 2001/0051158 published Dec. 13, 2001, Owens et al. describe immunochemical haptens which are meta-position derivatives of methamphetamine. The free amino group on the methamphetamine hapten is unprotected.

SUMMARY OF THE INVENTION

Compounds of the present invention are methamphetamine derivatives having a meta-substituted alkyl linker on the benzene ring and a protective group on the nitrogen of the methamphetamine hapten. Such compounds have the structure

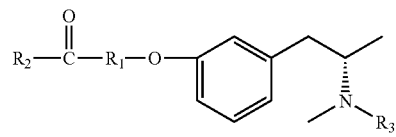

wherein $R_1$ is an alkyl linker comprising 2-15 carbon atoms and 0-6 heteroatoms, $R_2$ is a leaving group, and $R_3$ is a protecting group.

A preferred compound of the invention is 4-{[4-(3-{(S)-2-[methyl-(2,2,2-trifluoro-acetyl)-amino]-propyl}-phenoxy)-butyrylamino]-methyl}-benzoic acid 2,5-dioxo-pyrrolidin-1-yl ester having the structure

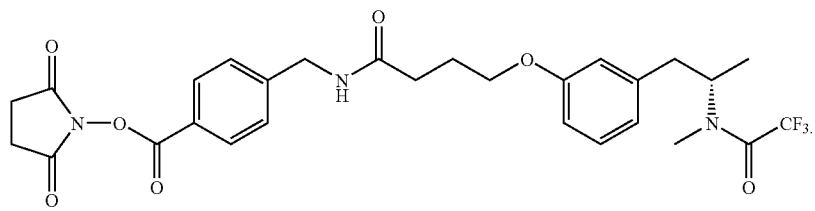

This compound, when conjugated to aminodextran followed by deprotection of the N-trifluoroacetate group, provides a conjugate that, when used in an immunoassay wherein it competes with free methamphetamine for binding to a methamphetamine-specific antibody immobilized on a microparticle, provides a standard curve having a good fit with the corresponding amphetamine-aminodextran-antibody system.

DETAILED DESCRIPTION OF THE INVENTION

Figure 1:
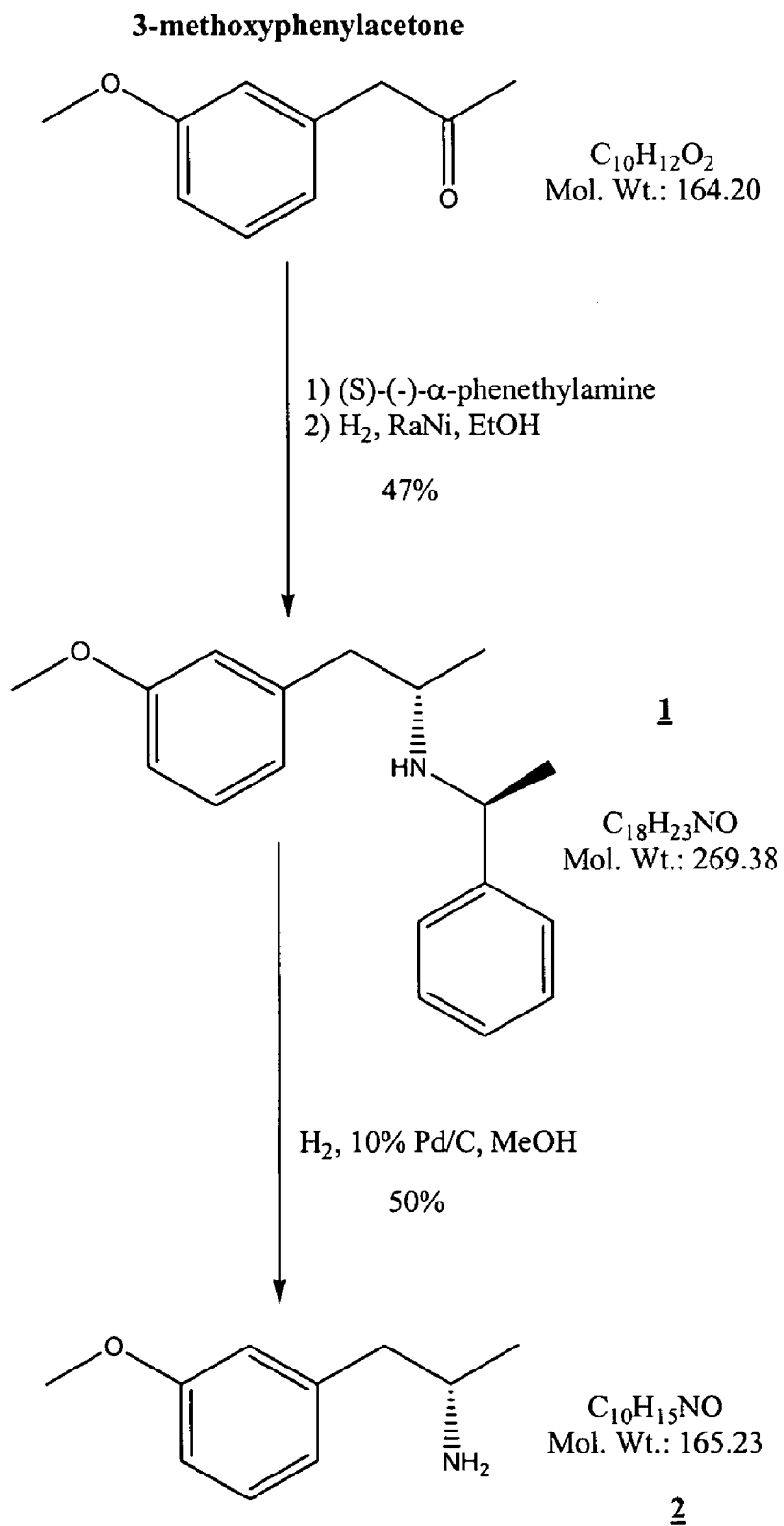
FIG. 1 is a schematic representation showing synthesis of (2) as described in Example 2.
Figure 2:
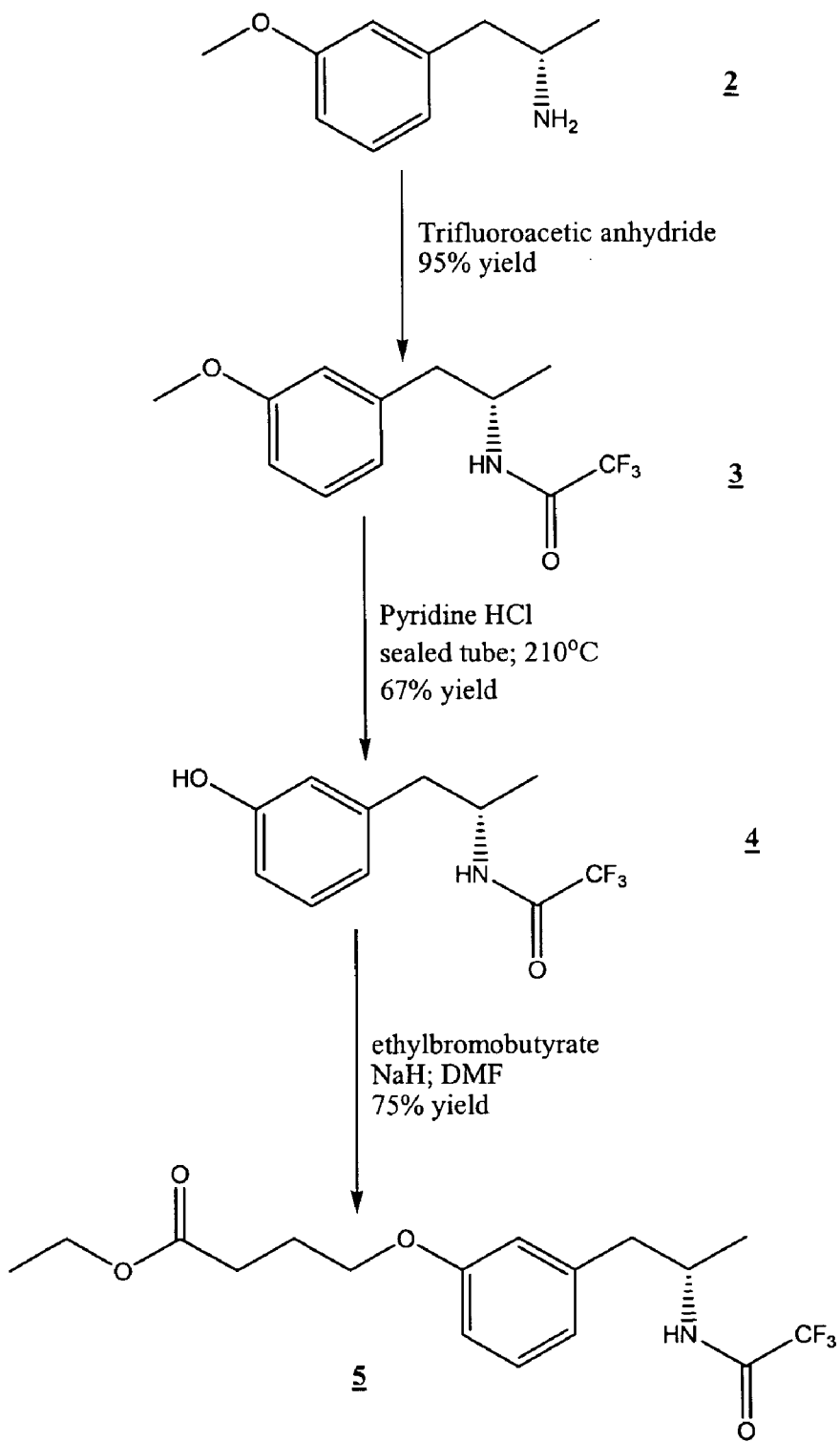
FIGS. 2 and 3 are schematic representations of the synthesis of a compound of the present invention, 4-(3-{(S)-2-[(2,2-dimethyl-propionyl)-methyl-amino]-propyl}-phenoxy)-butyric acid 2,5-dioxo-pyrrolidin-1-yl ester (8).
Figure 3:
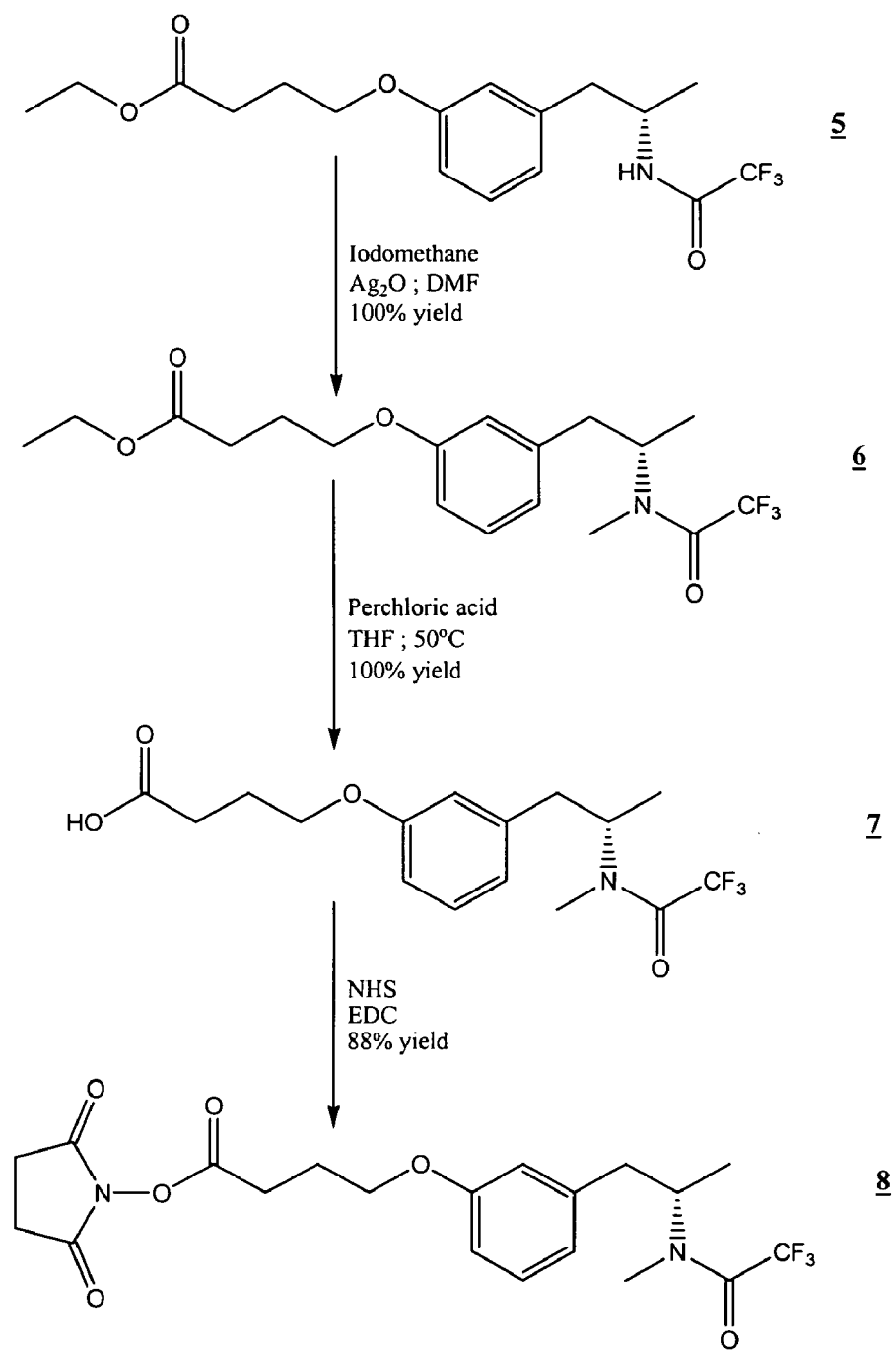
Figure 4:
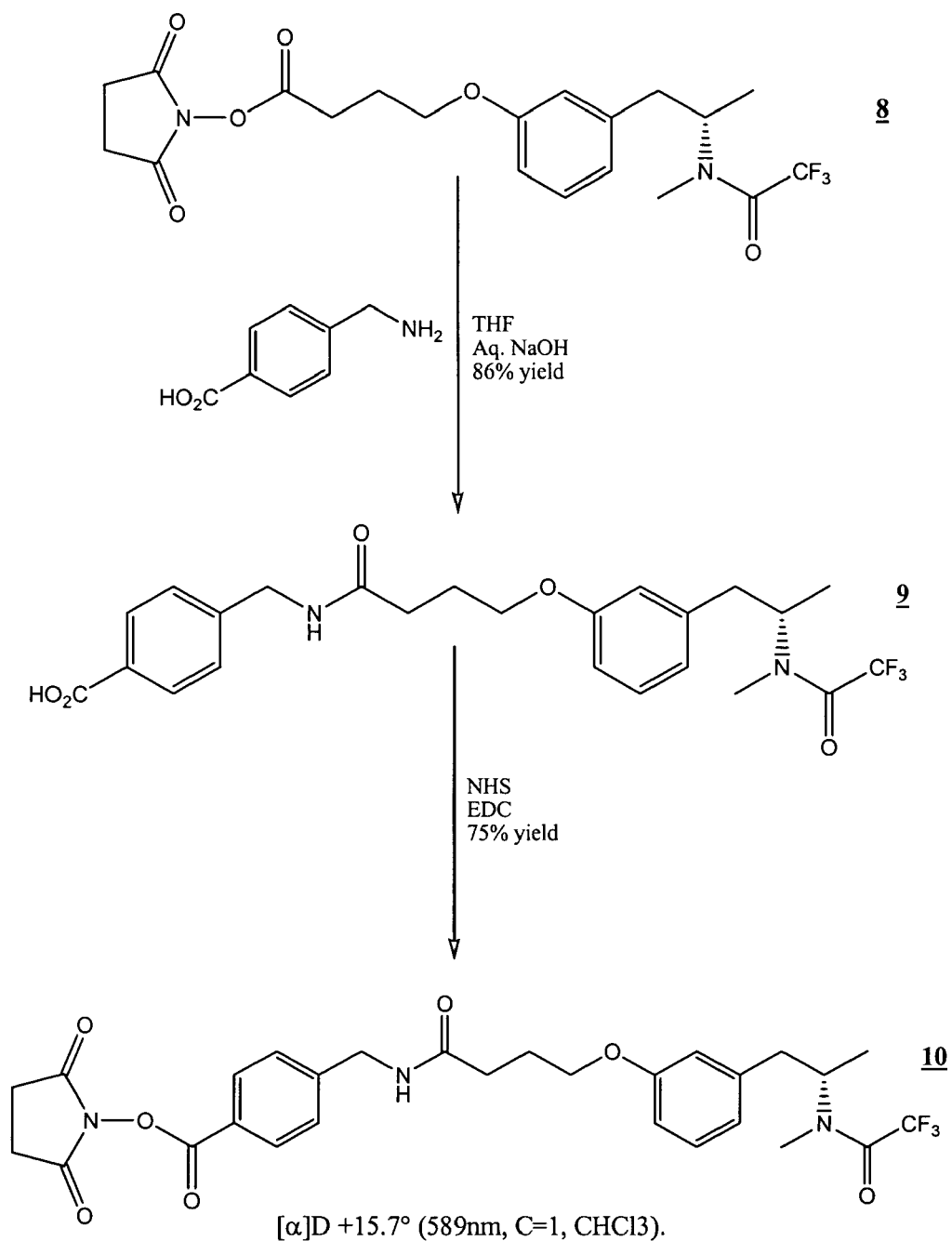
FIG. 4 is a schematic representation showing synthesis of 4-{[4-(3-{(S)-2-[methyl-(2,2,2-trifluoro-acetyl)-amino]-propyl}-phenoxy)-butyrylamino]-methyl}-benzoic acid 2,5-dioxo-pyrrolidin-1-yl ester (10) as described in Example 10.
Figure 5:
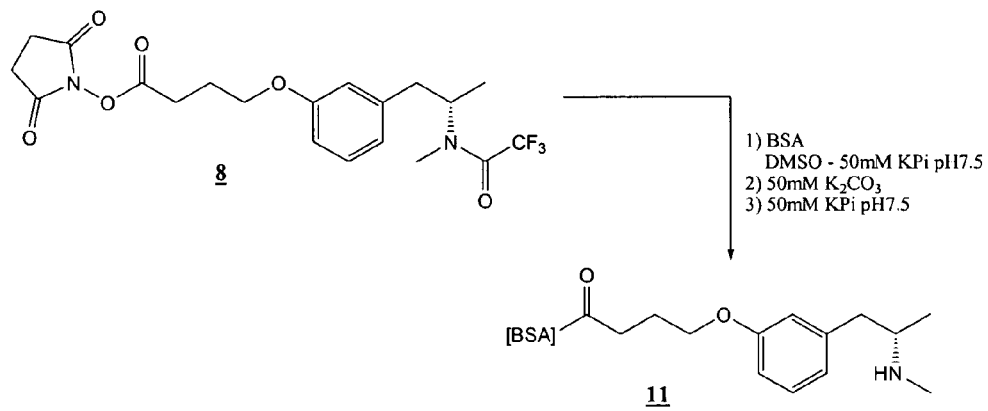
FIG. 5 is a schematic representation showing conjugation of a compound of the present invention with BSA and deprotection of the nitrogen to give (11) as described in Example 11.
Figure 6:
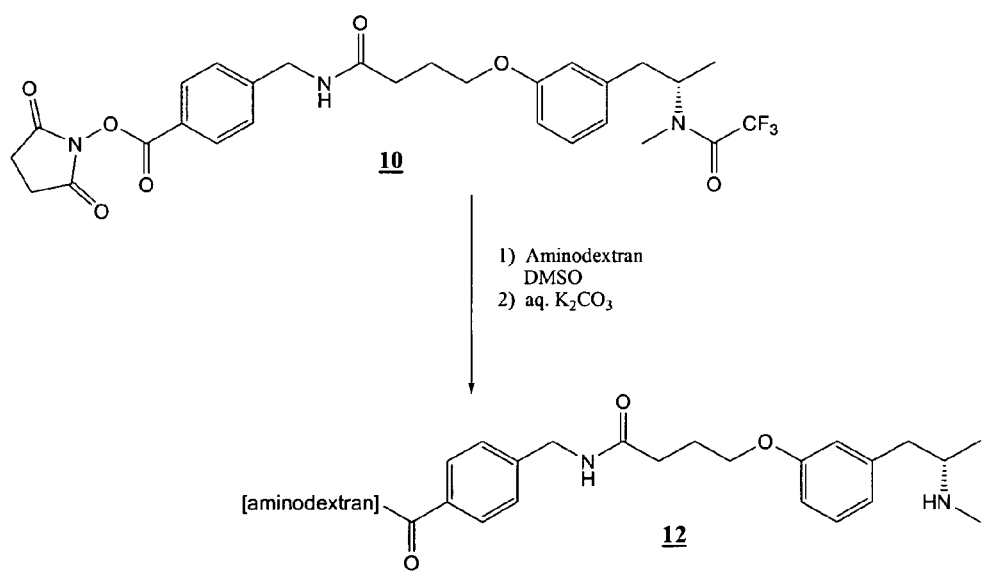
FIG. 6 is a schematic representation showing conjugation of a compound of the present invention with aminodextran followed by deprotection of the N-trifluoroacetate group.
Figure 7:
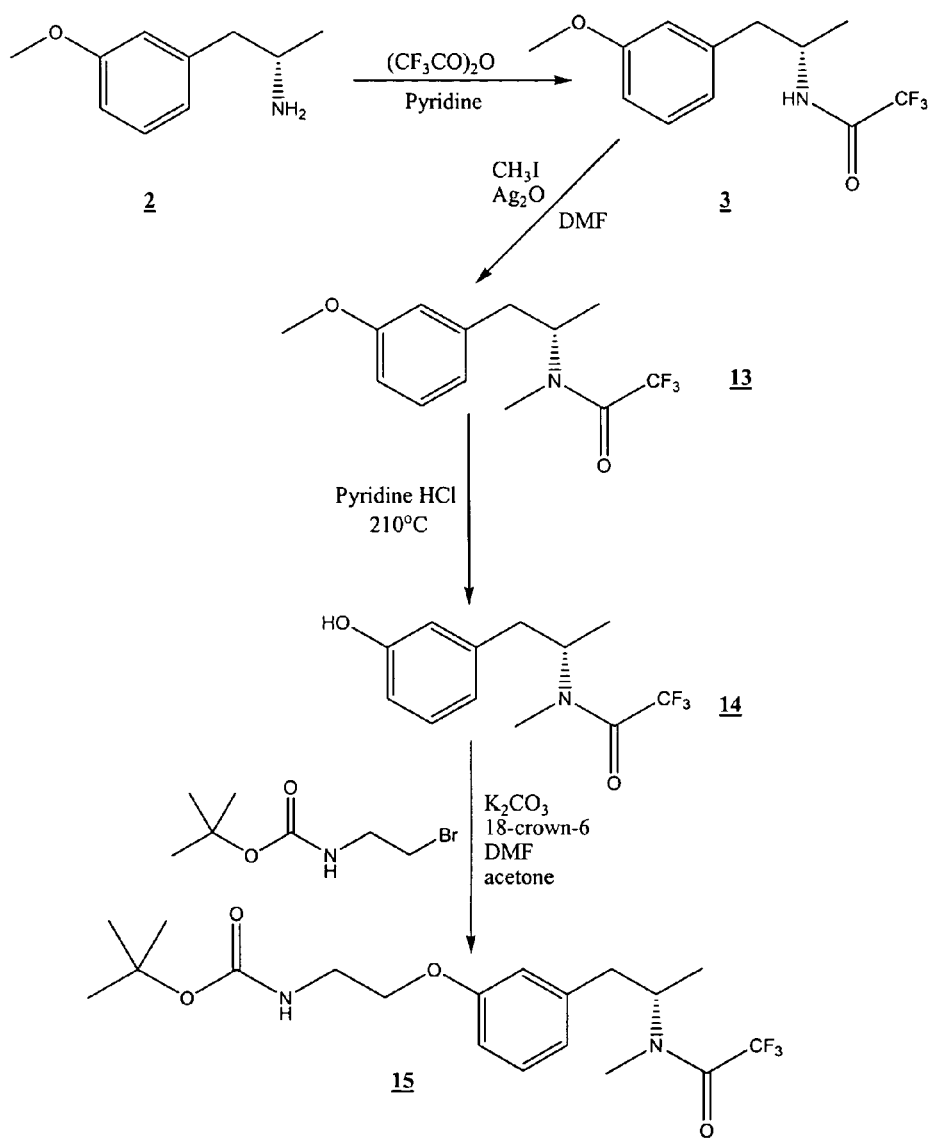
FIG. 7 is a schematic representation showing synthesis of (15) as described in Example 12.
Figure 8:
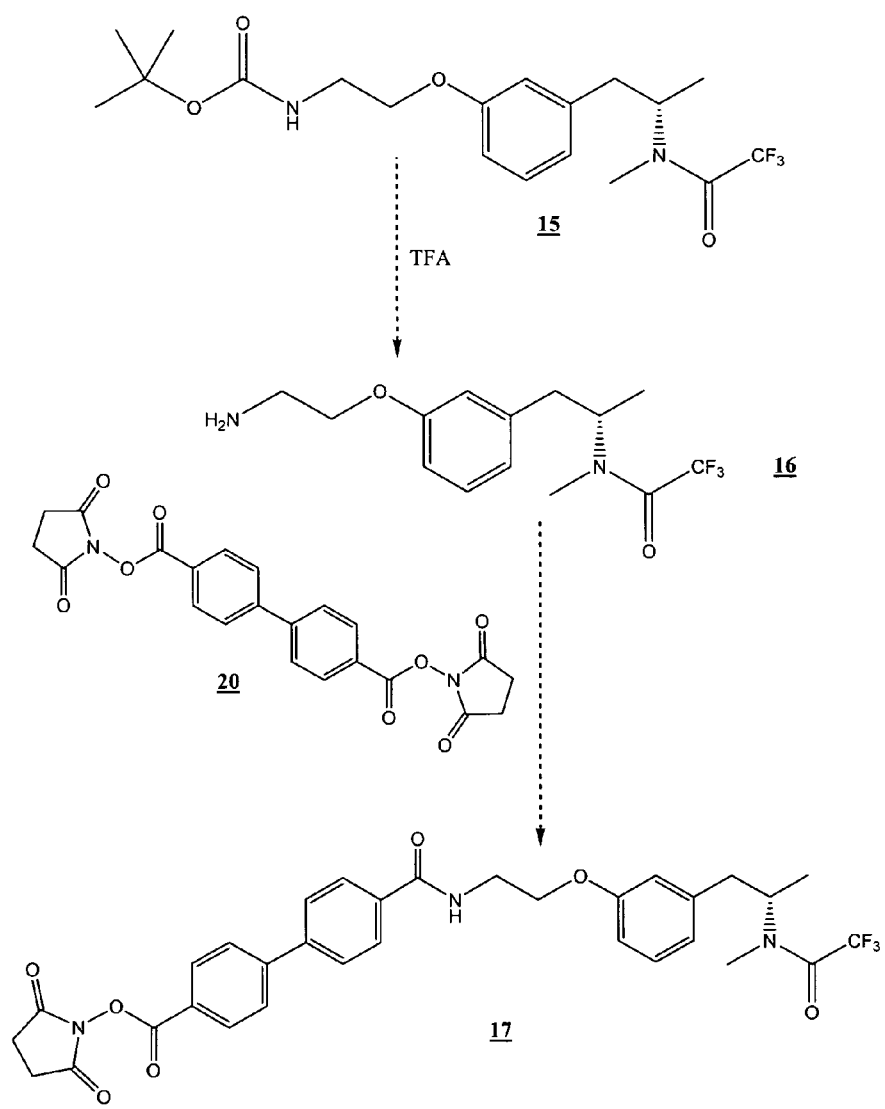
FIG. 8 is a schematic representation showing synthesis of (17) as described in Example 13.
Figure 9:
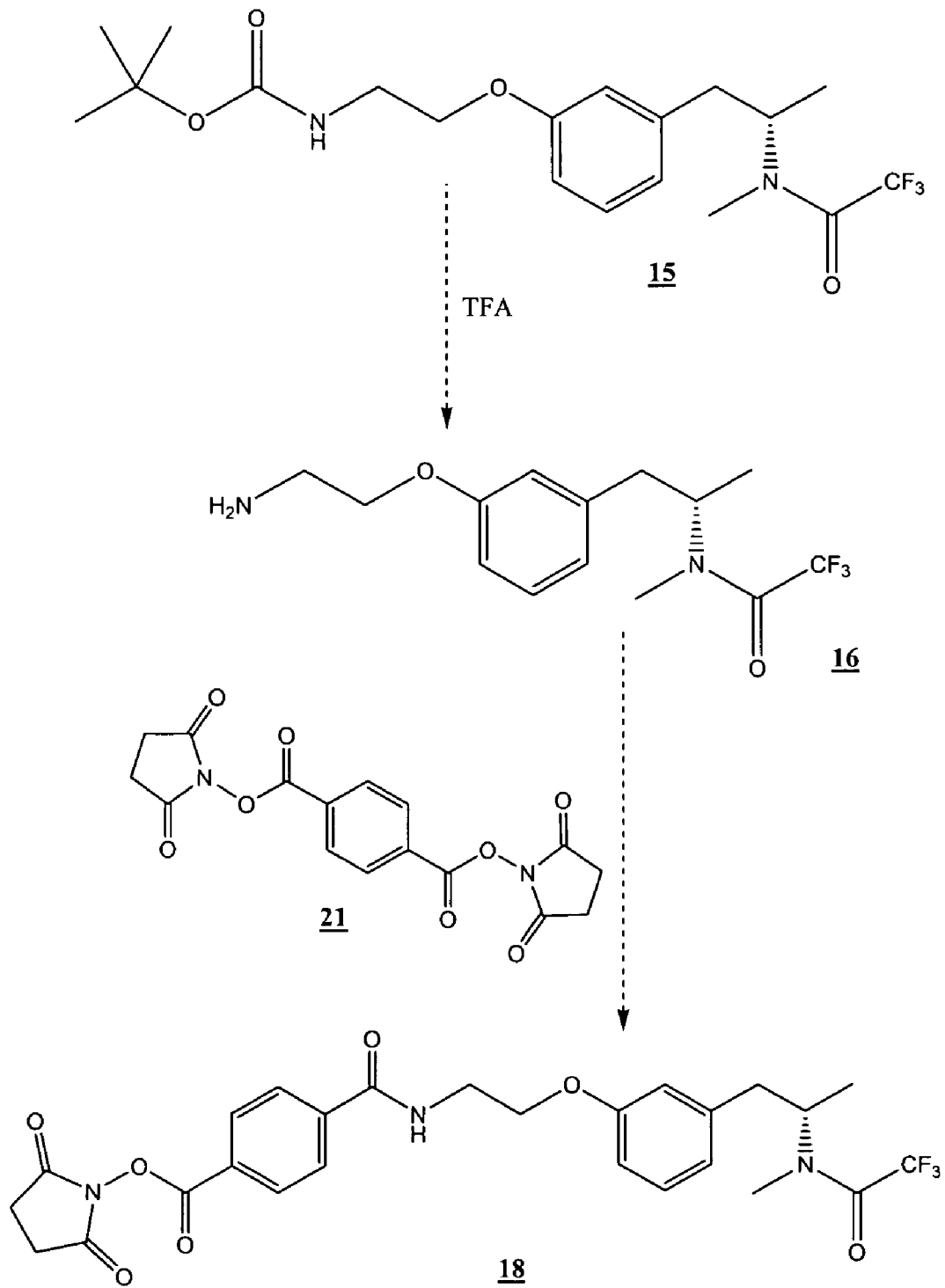
FIG. 9 is a schematic representation showing synthesis of (18) as described in Example 14.
Figure 10:
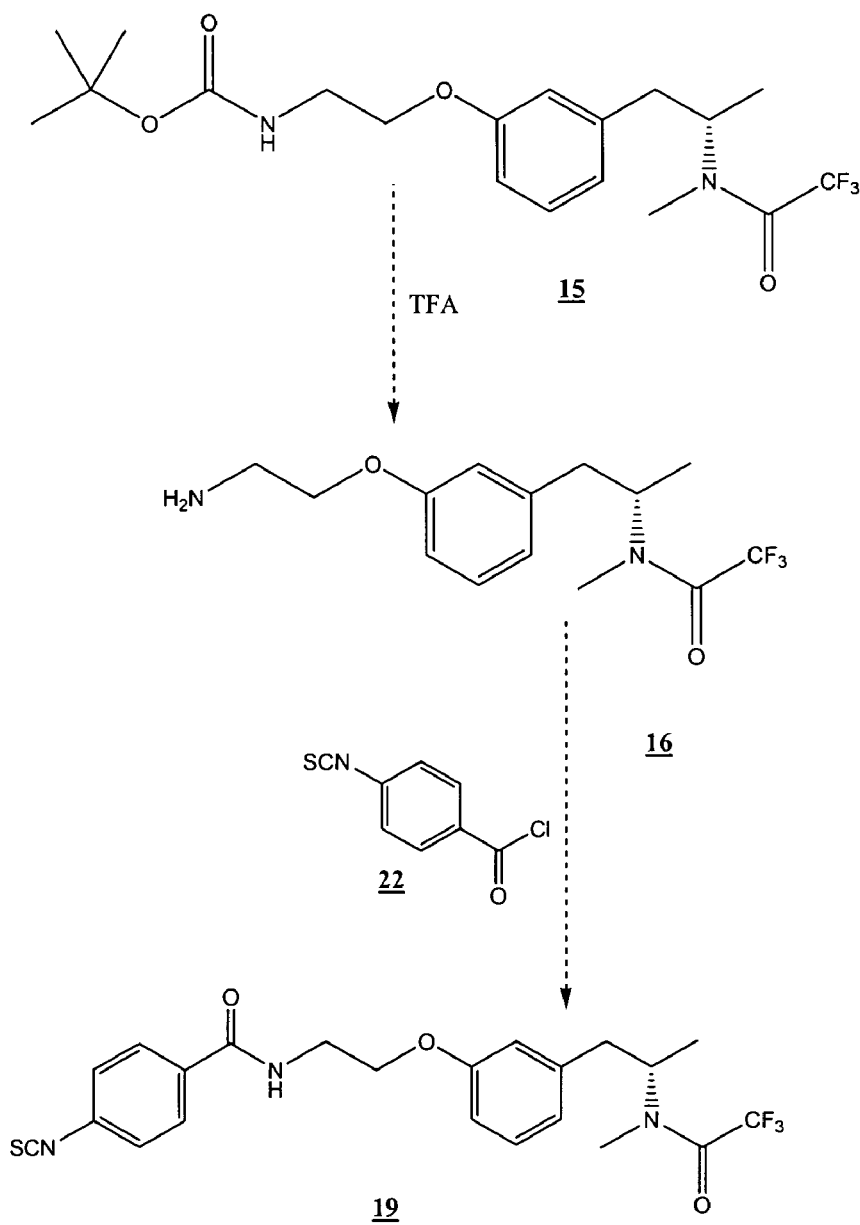
FIG. 10 is a schematic representation showing synthesis of (19) as described in Example 15.

Throughout this description and in the appended claims, the following definitions are to be understood.

The term "hapten" refers to a partial or incomplete antigen. Haptens are protein-free substances, mostly low molecular weight substances, which are not capable of stimulating antibody formation but which do react with antibodies. Amphetamine, methamphetamine, methylenedioxymethamphetamine, and other amphetamine-class compounds are haptens.

The term "activated hapten" refers to a hapten that has been provided with an available reaction site, for example, by the attachment of a linking group carrying a reactive moiety, that can be used to connect the hapten to a carrier, immunogen, label, tracer or other moiety.

The term "analyte" refers to any substance or group of substances, the presence or amount of which is to be determined. As used herein, the term analyte subsumes the term "antigen," which refers to any compound that can bind to an antibody.

The terms "amphetamine" and "amphetamine-class drugs" as used herein refer to amphetamine, methamphetamine, amphetamine analogues of methylenedioxyphenylalkylamines, also known as "designer" amphetamines, e.g., methylenedioxymethamphetamine (MDMA, also known as Ecstasy), and metabolites of these drugs.

The term "derivative" refers to a chemical compound or molecule made from a parent compound by one or more chemical reactions.

The term "conjugate" refers to any substance formed from the joining together of two parts. Representative conjugates in accordance with the present invention include those formed by the joining together of a small molecule and a large molecule, such as a protein. The term conjugate subsumes the term immunogen.

As used herein, a "linking group" or "linker" refers to a portion of a chemical structure which connects two or more substructures such as haptens, carriers, immunogens, labels, tracers or other linkers. A linking group has at least 1 uninterrupted chain of atoms other than hydrogen (or other monovalent atoms) extending between the substructures. The atoms of a linking group and the atoms of a chain within a linking group are themselves connected by chemical bonds. Linkers may be straight or branched, saturated or unsaturated, carbon chains. They may also include one or more heteroatoms within the chain or at termini of the chains. By "heteroatoms" is meant atoms other than carbon which are chosen from the group consisting of oxygen, nitrogen and sulfur. Linking groups may also include cyclic or aromatic groups as part of the chain or as a substitution on one of the atoms in the chain.

The number of atoms in a linking group or linker is determined by counting the atoms other than hydrogen. The number of atoms in a chain within a linking group is determined by counting the number of atoms other than hydrogen along the shortest route between the substructures being connected. Linking groups may be used to activate, e.g., provide an available site on a hapten for synthesizing a conjugate of a hapten with a label or carrier.

The term "alkyl group" refers to any straight, branched, cyclic, acyclic, saturated or unsaturated carbon chain. Representative alkyl groups include alkanes, alkenes, alkynes, cycloalkanes, cycloalkenes, cycloalkynes, aryls, and the like, and combinations thereof.

The phrase "optionally substituted" refers to the optional attachment of one or more substituents onto an alkyl group.

The term "leaving group" refers to any chemical moiety of a substrate that can be displaced by a reagent reacted therewith. Suitable leaving groups include, but are not limited to, halides, mesylates, tosylates, alkoxys, quaternary ammonium salts, and the like. Preferred leaving groups for use in accordance with the presently preferred embodiments are provided by activated esters, e.g., trifluoroethoxy esters, N-hydroxysuccinimide esters, p-nitrophenyl esters, pentafluorophenyl esters, imidazolyl esters, and N-hydroxybenzotriazolyl esters, whereby the oxygen-containing portion of the ester that is attached to the carbonyl carbon is displaced in the course of the reaction.

The term "protecting group" refers to any moiety that is attached to a reactive atom or center in order to alter its usual reactivity. Suitable protecting groups include but are not limited to those described in the treatise entitled *Protective Groups in Organic Synthesis*, $3^{rd}$ Edition by Theodora W. Greene and Peter G. M. Wuts (John Wiley & Sons, Inc., New York, 1999). Various protecting groups for the nitrogen of amines are known in the art, among which trifluoroacetyl is a presently preferred nitrogen protecting group. Examples of other preferred protecting groups include t-Boc (tert-butyloxycarbonyl) and CBZ (benzyloxycarbonyl).

The term "analyte analog" refers to any substance or group of substances, such as may be employed in a competitive immunoassay, which behaves similarly to an analyte with respect to binding affinity to an antibody. Representative analyte analogs include drugs and isomers thereof, drug derivatives, hormones, polypeptides, nucleotides, and the like.

The phrase "detecting an analyte" refers to any quantitative, semi-quantitative, or qualitative method, as well as to all other methods for determining an analyte in general, and an amphetamine drug in particular. For example, a method that merely detects the presence or absence of an amphetamine drug in a sample lies within the scope of the present invention, as do methods that provide data as to the amount or concentration of the drug in the sample. The terms detecting, determining, identifying, and the like are used synonymously herein, and all are within the scope of the present invention.

A "label", "detector molecule", or "tracer" is any molecule which produces, or can be induced to produce, a detectable signal. The label can be conjugated to an analyte, immunogen, antibody, or to another molecule such as a receptor or a molecule that can bind to a receptor such as a ligand, particularly a hapten. Non-limiting examples of labels include radioactive isotopes, enzymes, enzyme fragments, enzyme substrates, enzyme inhibitors, coenzymes, catalysts, fluorophores, dyes, chemiluminescers, luminescers, sensitizers, non-magnetic or magnetic particles, solid supports, liposomes, ligands, and receptors.

The term "reagent kit," or "test kit," refers to an assembly of materials that are used in performing an assay. The reagents can be provided in packaged combination in the same or in separate containers, depending on their cross-reactivities and stabilities, and in liquid or in lyophilized form. The amounts and proportions of reagents provided in the kit can be selected so as to provide optimum results for a particular application. A reagent kit embodying features of the present invention comprises antibodies specific for amphetamine compounds. The kit may further comprise ligands of the analyte and calibration and control materials. The reagents may remain in liquid form or may be lyophilized.

The phrase "calibration and control materials" refers to any standard or reference material containing a known amount of an analyte to be measured. A sample suspected of containing an analyte and the corresponding calibration material are assayed under similar conditions. The concentration of analyte is calculated by comparing the results obtained for the unknown specimen with the results obtained for the standard. This is commonly done by constructing a calibration or dose response curve.

Compounds of the present invention are methamphetamine derivatives having a meta-substituted alkyl or alkoxy linker on the benzene ring and a protective group at the nitrogen. Such compounds have the structure

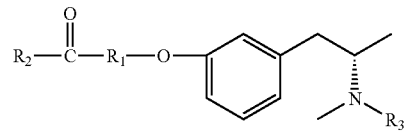

wherein $R_1$ is an alkyl linker comprising 2-15 carbon atoms and 0-6 heteroatoms, $R_2$ is a leaving group, and $R_3$ is a protecting group.

A preferred compound of the invention has the structure

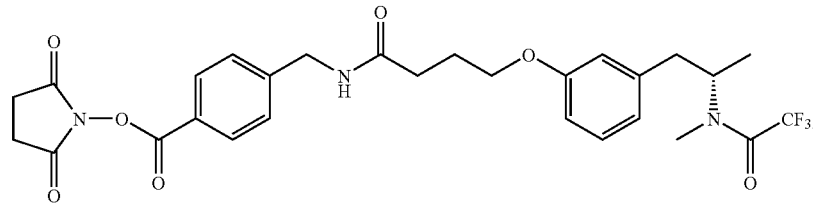

Such a compound, when conjugated to carrier molecules such as aminodextran followed by deprotection of the N-trifluoroacetate group, provides a conjugate that, when used in an immunoassay method wherein the conjugate competes with free methamphetamine for binding to a methamphetamine-specific antibody immobilized on a microparticle, provides a standard curve having good correlation with the corresponding amphetamine-aminodextran-antibody system. The combination also provides suitable cross reactivities with both desired (high cross reactivity) and undesired (low cross reactivity) analytes. When conjugated to bovine serum albumin at a low substitution ratio, such a compound also furnishes a conjugate suitable for the screening of methamphetamine antibodies.

The derivatives carry a protective group at the nitrogen. Such a protective group allows for the easy reaction of the active ester moiety of the derivatives with, typically, amines of carrier compounds to form stable amide bonds without the amine of the derivative itself interfering. The protective group is then subsequently readily removed to provide the desired unprotected amine moiety corresponding to the amine of the free drug.

The position of substitution and ether linkage of the linking group were also found to be advantageous in moderating the affinity of the antibody for the derivative conjugate, while the use of the aminomethylbenzoate moiety also aids in both easier characterization of the derivative (greater UV absorbance) as well as enhancing the solid nature of the derivatives (as opposed to gums or liquids).

It was quite surprisingly found that the derivative of the present invention is recognized by two antibodies raised in response to immunogens which are structurally quite distinct from the novel derivative. One difference is the position of substitution, which is para in the two immunogens but meta in the conjugate. Another difference is that the linker used for the immunogens does not have an oxygen atom coming off the benzene ring as does the conjugate. Finally, the nitrogen in the immunogens is bonded to a methyl group whereas the nitrogen in the conjugate of the invention is bonded to an ethyl group.

SPECIFIC EMBODIMENTS

In the examples that follow, boldface numbers refer to the corresponding structure in the drawings.

Flash chromatography was carried out on silica gel 60 (230-400 mesh, EM Science). Thin layer chromatography was performed on silica gel plates (0.25 mm, EM Science, Cat #5717-5) and visualized under an ultraviolet lamp.

Solvents were obtained from J.T. Baker Company unless otherwise stated. Ethyl acetate (EtOAc), hexanes (Hex) methanol (MeOH), and methylene chloride ($CH_2Cl_2$) were used as received for chromatography and reaction work-ups. Dry $CH_2Cl_2$ was obtained by boiling over calcium hydride under argon and under reflux. Dry tetrahydrofuran (THF) was obtained by boiling over sodium-benzophenone under argon and under reflux. Dry dimethylformamide (DMF) and dry dimethylsulfoxide (DMSO) were obtained in Sure/Seal™ bottles from Aldrich Chemical Company.

Reagents and chemicals were obtained from either Sigma-Aldrich Chemical Company or from Fluka Chemicals unless otherwise stated.

Proton nuclear magnetic resonance spectra ($^1$H-NMR) were obtained on a Varian Gemini 2000 (200 MHz) equipped with a Sun/Sparc work station. Optical rotations were performed on a Perkin Elmer 341 polarimeter.

3N perchloric acid was prepared by diluting 70% perchloric acid (11.7N)

Liquid chromatography mass spectra (LC-MS) and high performance liquid chromatography spectra (HPLC) were obtained on an Agilent HP1100 LC/MS system equipped with a diode array detector and quaternary pump. For LC-MS spectra/analyses, the chromatographic stream was ported post-column into the MSD detector. Unless otherwise stated, the analytical column used was a Vydac 218TP54 analytical column (300 Å, 5 μ) equipped with a Phenomenex guard module (KJO-4282). Unless otherwise stated, runs were performed using 0.1% TFA-MeCN (C) in 0.1% TFA-$H_2O$ (A) with a solvent gradient of 5% (0 min) to 100% (20 min) to 5% (25 min) of (C) in (A).

EXAMPLE 1

Synthesis of compound (1), [(S)-2-(3-methoxy-phenyl)-1-methyl-ethyl]-((S)-1-phenyl-ethyl)-amine A solution of 6.0 g (0.0365 mol) of 3-methoxyphenylacetone (Trans World Chem.) and 4.47 g (0.0369 mol) of S-(−)-α-phenylethylamine (Fluka) in 100 ml of benzene (Acros) was treated with 6.0 g of 4 Å molecular sieves and heated to reflux for 3 hrs. The mixture was filtered and concentrated at reduced pressure. The residue was dissolved in 100 ml of absolute ethanol (Aldrich), placed in a 500 ml Parr bottle containing 2.4 g of Raney nickel (50% slurry in $H_2O$) and hydrogenated at 50 PSI for 24 hrs. The catalyst was filtered off through CELITE and the filtrate was concentrated at reduced pressure. The residue was purified by flash chromatography on 800 g of silica gel using 3% methanol-$CH_2Cl_2$ as eluent to yield 5.0 g of product as a pale yellow oil. $^1$H-NMR ($CDCl_3$) compatible; LC-MS: $t_R$ 11.4 min, observed M+H 270.2; $[\alpha]_D$ −36.6° (589 nm, c=1, $CHCl_3$).

EXAMPLE 2

Synthesis of compound (2), (S)-2-(3-methoxy-phenyl)-1-methyl-ethylamine

A 500 ml Parr bottle was charged with 550 mg of 10% Pd/C and a solution of 5.0 g (0.0186 mol) of compound (1) in 100 ml of methanol and hydrogenated at 50 PSI for 48 hrs. The catalyst was filtered off through CELITE and the filtrate was concentrated at reduced pressure to a yellow oil. This was purified by flash chromatography on a short column of silica gel (4 cm W, 5 cm H) using 10% methanol-$CH_2Cl_2$ to remove residual catalyst to yield 2.84 g of yellow oil. This was dissolved in $CH_2Cl_2$ and filtered to remove residual silica gel, then concentrated at reduced pressure and pumped at high vacuum overnight to yield 2.5 g of yellow oil. $^1$H-NMR ($CDCl_3$) compatible; LC-MS: $t_R$ 8.05 min (Chiralcel OD-RH, Daicel Chemical Industries; gradient of 5% (at 0 min) to 85% (at 17.5 min) of 0.1% TFA/acetonitrile in 0.1% TFA/water; 0.5 mL/min flow rate), observed M+H 166.1, one peak; HPLC: $t_R$ 30.0 min (d-isomer), 33.7 min (l-isomer), ratio d/l=97.2/2.8 at 200 nm (Crownpak CR(+), Daicel Chemical Industries; isocratic 1 ml/min of aq perchloric acid pH 1.35 (~0.2%) containing 5% MeOH); $[\alpha]_D$ +31.7° (589 nm, c=1, $CHCl_3$).

EXAMPLE 3

Synthesis of compound (3), 2,2,2-trifluoro-N-[(S)-2-(3-methoxy-phenyl)-1-methyl-ethyl]-acetamide A solution of 2.4 g (0.0145 mol) of compound (2) in 24 ml of pyridine (Aldrich) under argon was cooled to −20° C. and treated with a solution of 3.2 ml of trifluoroacetic anhydride in 36 ml of ether (E. M. Science) and stirred at −20° C. for 15 min. The mixture was extracted with 3×100 ml of ethyl acetate. The combined ethyl acetate extracts were washed with 2×150 ml of saturated brine solution, dried over anhydrous $Na_2SO_4$ and concentrated at reduced pressure to yield 3.79 g of yellow solid. $^1$H-NMR ($CDCl_3$) compatible.

EXAMPLE 4

Synthesis of compound (4), 2,2,2-trifluoro-N-[(S)-2-(3-hydroxy-phenyl)-1-methyl-ethyl]-acetamide A pressure bomb containing 3.77 g (0.0144 mol) of compound (3) and 70.0 g (0.6057 mol) of pyridine-HCl was purged with argon and heated at 210° C. for 45 min. The solids melted and became homogeneous. The reaction mixture was allowed to cool, at which time it solidified. The solid was dissolved in $H_2O$ and poured into 400 ml of ice water. This was extracted with 5×250 ml of $CH_2Cl_2$. The $CH_2Cl_2$ extracts were combined, dried over anhydrous $Na_2SO_4$ and concentrated at reduced pressure, then pumped at high vacuum overnight to yield 3.34 g of yellow oil. $^1$H-NMR (CDCl$_3$) compatible; LC-MS compatible.

In another run, similar reaction of 320 mg of compound (3) and 5.94 g of pyridine hydrochloride in a pressure bomb gave, after similar work-up, 213 mg of compound (4) which had: $^1$H-NMR compatible; LC-MS: $t_R$ 11.4 min, observed M+H 248.1, M+Na 270.1.

EXAMPLE 5

Synthesis of compound (5), 4-{3-[(S)-2-(2,2,2-trifluoro-acetylamino)-propyl]-phenoxy}-butyric acid ethyl ester A mixture of 1.08 g (0.027 mol) of NaH (60% dispersion in mineral oil) and 10 ml of anhydrous DMF (Aldrich) under argon was treated with a solution of 3.3 g (0.0133 mol) of compound (4) in 33 ml of anhydrous DMF (Aldrich) added dropwise over a 5 min. time period. The mixture was stirred at ambient temperature for 10 min. then treated with 3.4 ml (0.0238 mol) of ethyl-4-bromobutyrate (Fluka) and stirred at room temperature overnight. The mixture was poured into 250 ml of 1M potassium phosphate buffer pH 7, then extracted with 2×250 ml of ethyl acetate. The organic extracts were combined and washed with 2×150 ml of 1M potassium phosphate buffer pH 7, dried over anhydrous $Na_2SO_4$ and conc. at reduced pressure. The residue was purified by flash chromatography on 250 g of silica gel using 30% EtOAc-hexane as eluent to yield a pale yellow oil which crystallized on standing to yield 3.9 g of a white solid. $^1$H-NMR (CDCl$_3$) compatible; LC-MS: $t_R$ 15.7 min, observed M+H 362.1, M+H$_2$O 379.1, M+Na 384.1.

EXAMPLE 6

Synthesis of compound (6), 4-(3-{(S)-2-[methyl-(2,2,2-trifluoro-acetyl)-amino]-propyl}-phenoxy)-butyric acid ethyl ester A solution of 3.8 g (0.0105 mol) of compound (5) in 72 ml of anhydrous DMF (Aldrich) under argon was treated with 9.5 ml (0.1526 mol) of iodomethane and 11.74 g (0.0507 mol) of silver (I) oxide and stirred at 40° C. overnight. The mixture was filtered through CELITE, the filter cake was washed with 450 ml of ethyl acetate, and the filtrate was filtered again to remove a white precipitate. The filtrate was washed with 2×250 ml of $H_2O$. The $H_2O$ washes were combined and extracted with 200 ml of ethyl acetate. The organic extracts were combined, dried over anhydrous $Na_2SO_4$, concentrated at reduced pressure and pumped at high vacuum overnight to yield 3.84 g of pale yellow oil. $^1$H-NMR (CDCl$_3$) compatible, ~2:1 ratio of rotamers.

EXAMPLE 7

Synthesis of compound (7), 4-(3-{(S)-2-[methyl-(2,2,2-trifluoro-acetyl)-amino]-propyl}-phenoxy)-butric acid A solution of 3.8 g (00101 mol) of compound (6) in 50 ml of distilled THF was treated with 50 ml of 3N perchloric acid (prepared from 70% perchloric acid obtained from Aldrich) and heated at 50° C. for 4 hrs. The mixture was cooled and extracted with 2×200 ml of ethyl acetate. The organic extracts were combined, washed with 4×200 ml of $H_2O$, 2×200 ml of saturated brine solution, dried over anhydrous $Na_2SO_4$, concentrated at reduced pressure and pumped at high vacuum overnight to yield 3.5 g of pale yellow oil. $^1$H-NMR (CDCl$_3$) compatible, ~2:1 ratio of rotamers.

EXAMPLE 8

Synthesis of compound (8), 4-(3-{(S)-2-[(2,2-dimethyl-propionyl)-methyl-amino]-propyl}-phenoxy)-butyric acid 2,5-dioxo-pyrrolidin-1-yl ester A solution of 3.5 g (0.0101 mol) of compound (7) in 220 ml of anhydrous $CH_2Cl_2$ under argon was treated with 1.4 g (0.0122 mol) of NHS and 2.4 g (0.0125 mol) of EDC (Sigma) and stirred at room temperature overnight. The mixture was washed with 200 ml of 0.1N HCl, 2×200 ml of $H_2O$, 2×200 ml of saturated NaHCO$_3$ solution, 200 ml of saturated brine solution, dried over anhydrous $Na_2SO_4$ and concentrated at reduced pressure to yield 4.42 g of clear oil. $^1$H-NMR (CDCl$_3$) compatible, ~3:2 ratio of rotamers.

EXAMPLE 9

Synthesis of compound (9), 4-{[4-(3-{(S)-2-[methyl-(2,2,2-trifluoro-acetyl)-amino]-propyl}-phenoxy)-butyrylamino]-methyl}-benzoic acid A mixture of 1.6 g (0.0106 mol) of 4-aminomethylbenzoic acid in 60 ml of $H_2O$ and 120 ml distilled THF was treated with 10 ml of 1N NaOH. The resulting solution was then treated with a solution of 4.4 g (0.01 mol) of compound (8) in 120 ml of distilled THF. The reaction was then treated with 4 ml of 1N NaOH added 1 ml at a time to maintain pH 9. The reaction was stirred at room temperature for 1 hr. The THF was removed at reduced pressure and the aqueous residue was neutralized to pH 6 with 2N HCl. This was extracted with 2×250 ml of ethyl acetate. The organic extracts were combined, dried over anhydrous $Na_2SO_4$ and concentrated at reduced pressure to yield 4.65 g of white solid. $^1$H-NMR (CDCl$_3$) compatible, ~3:2 ratio of rotamers.

EXAMPLE 10

Synthesis of compound (10), 4-{[4-(3-{(S)-2-[methyl-(2,2,2-trifluoro-acetyl)-amino]-propyl}-phenoxy)-butyrylamino]-methyl}-benzoic acid 2,5-dioxo-pyrrolidin-1-yl ester A solution of 1.0 g (0.002 mol) of compound (9) in 100 ml of anhydrous $CH_2Cl_2$ under argon was treated with 300 mg (0.0026 mol) of NHS and 480 mg (0.0025 mol) of EDC (Sigma) and stirred at room temperature overnight. The mixture was washed with 100 ml of 0.1N HCl, 2×100 ml of $H_2O$, 2×100 ml of saturated NaHCO$_3$ solution, 100 ml of saturated brine solution, dried over anhydrous $Na_2SO_4$ and concentrated at reduced pressure to yield 1.13 g of white amorphous solid. $^1$H-NMR (CDCl$_3$) compatible, ~3:2 ratio of rotamers; LC-MS: $t_R$ 14.5 min, observed M+H 578.2, M+Na 600.2; $[\alpha]_D$ +15.7° (589 nm, c=1, $CHCl_3$).

EXAMPLE 11

Synthesis of compound (11), deprotected 4-(3-{(S)-2-[(2,2-dimethyl-propionyl)-methyl-amino]-propyl}-phenoxy)-butyric acid 2,5-dioxo-pyrrolidin-1-yl ester conjugate with BSA A solution of 1.0 g of bovine serum albumin (BSA; Pentex Fraction V; Miles Inc., Kankakee, Ill., USA) in 16 ml of 50 mM potassium phosphate (KPi) pH 7.5 was cooled in an ice bath and treated with 22 ml of DMSO added dropwise slowly. After addition was complete, a solution of 13.4 mg of compound (8) in 2 ml of DMSO was added dropwise and the reaction allowed to attain RT with stirring. A reference sample of 100 mg of BSA in 1.6 ml of 50 mM KPi pH 7.5 and 2.4 ml of DMSO was also prepared in a similar manner but no hapten was added. After stirring overnight both the reaction and reference sample were separately transferred to dialysis tubing (SpectraPor 7; 10,000 molecular weight cutoff) and dialyzed against 60% DMSO –50 mM KPi, pH 7.5 (twice at RT/4 h each; once at RT overnight) then sequentially against 40% to 20% to 10% DMSO –50 mM KPi, pH7.5, then against 50 mM KPi pH7.5. Dialysis was continued against 50 mM potassium carbonate (four changes) at RT for 4 d to deprotect the trifluoroacetyl group, then against 50 mM KPi pH7.5 at ~4° C. over several days (six changes). The retentates were recovered to give the conjugate (11) as a grayish solution (68 ml), as well as the reference BSA. Coomassie Blue protein assay, using the reference BSA [protein concentration by UV] to generate the standard curve, indicated 14.0 mg/ml protein for conjugate (11).

EXAMPLE 12

Synthesis of compound (15), [2-(3-{(S)-2-[methyl-(2,2,2-trifluoro-acetyl)-amino]-propyl}-phenoxy)-ethyl]-carbamic acid tert-butyl ester Compound (13), 2,2,2-trifluoro-N-[(S)-2-(3-methoxyphenyl)-1-methyl-ethyl]-N-methyl-acetamide. A solution of 384 mg of compound (3) in 10 ml of dry dimethylformamide (DMF) under argon was treated with 1.33 ml of iodomethane and 1.64 g of silver (I) oxide and stirred at 40° C. overnight. The mixture was filtered through CELITE and the filter cake washed with ethyl acetate. The filtrate was filtered again to remove a white precipitate. The filtrate was washed with 2×50 ml of $H_2O$. The aqueous washes were combined and extracted with 50 ml of ethyl acetate. The ethyl acetate portions were combined, dried over anhydrous sodium sulfate, and concentrated at reduced pressure to yield 330 mg of yellow oil. This was chromatographed on 50 g of silica gel using $CH_2Cl_2$ as eluent to yield 220 mg of the product, compound (13), as a pale yellow oil. LC-MS: $t_R$ 15.4 min, observed M+H 276.0, M+Na 298.0.

Compound (14), 2,2,2-trifluoro-N-[(S)-2-(3-hydroxyphenyl)-1-methyl-ethyl]-N-methyl-acetamide. A mixture of 220 mg of compound (13) and 3.87 g of pyridine hydrochloride were heated at 210° C. in a pressure bomb for 1 hr. The resulting melt was allowed to cool and was dissolved in water. This was extracted with 5×50 ml of $CH_2Cl_2$. The combined $CH_2Cl_2$ extracts were dried over anhydrous sodium sulfate and concentrated at reduced pressure to yield 100 mg of compound (14) as a yellow oil. LC-MS: $t_R$ 12.9 min, observed M+H 262.0, M+Na 284.0.

Compound (15). A solution of 25 mg of compound (14) in 10 ml of dry acetone was treated with a solution of 2-(BOC-amino)ethyl bromide in 1 ml of dry DMF, 77 mg of anhydrous potassium carbonate, and a catalytic amount of 18-crown-6. The mixture was heated at 60° C. overnight. The mixture was cooled and diluted with $CH_2Cl_2$, washed 3 times with $H_2O$, dried over anhydrous sodium sulfate, and concentrated at reduced pressure to a red oil containing compound (15). LC-MS: tR 16.5 min, observed M+Na 427.1.

EXAMPLE 13

Synthesis of Compound (17)

Compound (15) is treated with trifluoroacetic acid and stirred at room temperature for 2 hrs. The mixture is concentrated at reduced pressure to give the amine compound (16).

A solution of biphenyl-di-carboxylic acid NHS ester, compound (20) (Ghoshal et al., U.S. Pat. No. 6,794,496), in dry THF under argon is treated with a solution of 1 equivalent of compound (16) in dry THF with 2 equivalents of triethylamine added dropwise. The mixture is stirred at room temperature overnight. The mixture is concentrated at reduced pressure. Purification by chromatography gives compound (17).

EXAMPLE 14

Synthesis of Compound (18)

A solution of terephthalic acid di-(N-hydroxysuccinimide) ester compound (21) (Ghoshal et al., European Patent Application 1,148,339) in dry THF, under argon, is treated with a solution of 1 equivalent of compound (16) in dry THF with 2 equivalents of triethylamine added dropwise. The mixture is stirred at room temperature overnight. The mixture is concentrated at reduced pressure. Purification by chromatography gives compound (18).

EXAMPLE 15

Synthesis of Compound (19)

A solution of 4-isothiocyanatobenzoyl chloride, compound (22) (Ghoshal et al., U.S. Pat. No. 6,794,496), in dry THF under argon is cooled with an ice bath and is treated with a solution of 1 equivalent of compound (16) in dry THF with 2 equivalents of triethylamine added dropwise. The mixture is stirred at room temperature overnight. The mixture is concentrated at reduced pressure. Purification by chromatography gives compound (19).

EXAMPLE 16

Assay Using Conjugate of Present Invention with Methamphetamine Antibody

The methamphetamine-aminodextran conjugate, compound (12), was prepared as follows: Ninety mg of aminodextran were dissolved in 5 ml DMSO. Ten mg of compound (10) were dissolved in 1 ml DMSO and added dropwise to the solution of the polymer carrier and stirred at room temperature overnight. The mixture was placed into 10,000 MW cut-off dialysis tubing (Pierce Snakeskin™) and dialyzed in 1 liter of 80% DMSO overnight at room temperature. This was then dialyzed using a step-down gradient in 1 liter of 60% DMSO, 1 liter of 40% DMSO, 1 liter of 20% DMSO, 4 liters of deionized water, for at least 3 each at room temperature. This was then dialyzed with 1 liter of 100 mM $K_2CO_3$, adjusted to pH 13 with KOH, for 2 days with 4 changes of buffer. A final dialysis step included 4 liters of deionized water for at least 2 days with 4 changes. The conjugate was then lyophilized.

A conjugate reagent, pH 7.1, was then prepared containing 0.125 μg/ml methamphetamine conjugate (12), 144 mM piperazine-1,4-bis(2-ethanesulfonic acid) disodium salt, 31 mM piperazine-1,4-bis(2-ethanesulfonic acid), 0.1% (w/v) BSA, 0.09% (w/v) sodium azide, and 1.5% (w/v) polyacrylic acid.

An antibody-microparticle reagent was prepared as follows: 100 ml of 50 μg/ml monoclonal antibody specific for methamphetamine was incubated with 100 ml 1% 0.201 μm latex particles in 50 mM MES buffer, pH 6.5, overnight at room temperature. The particles were blocked with 10 ml of 100 mg/ml BSA in 50 mM MES buffer, pH 6.5, for 2 hours. Latex was washed with 50 mM MOPS buffer, pH 7.1, using tangential flow filtration system. This antibody was raised in response to the immunogen described in U.S. Pat. No. 5,501,987 (column 3, structure 2 where the protein is bovine thyroglobulin).

A microparticle reagent, pH 7.1, was then prepared containing 0.1% solids antibody-coated microparticles, 25 mM 3-morpholinopropanesulfonic acid, 25 mM 3-morpholinopropanesulfonic acid, sodium salt, 0.1% (w/v) BSA, and 0.09% (w/v) sodium azide.

The assay was carried out on a Roche/Hitachi 917 analyzer. Ten μl of sample was pipetted into a cuvette and was immediately followed by the addition of 180 μl conjugate reagent (R1). The mixture was incubated for ~90 seconds, and 80 μl of microparticle reagent (R2) were added to the cuvette. The reaction mixture was incubated at 37° C. for approximately 8 min, during which time the particle agglutination reaction was monitored at 505 nm. A standard curve was devised based on a 2-point end measurement after R2 addition.

Figure 11:
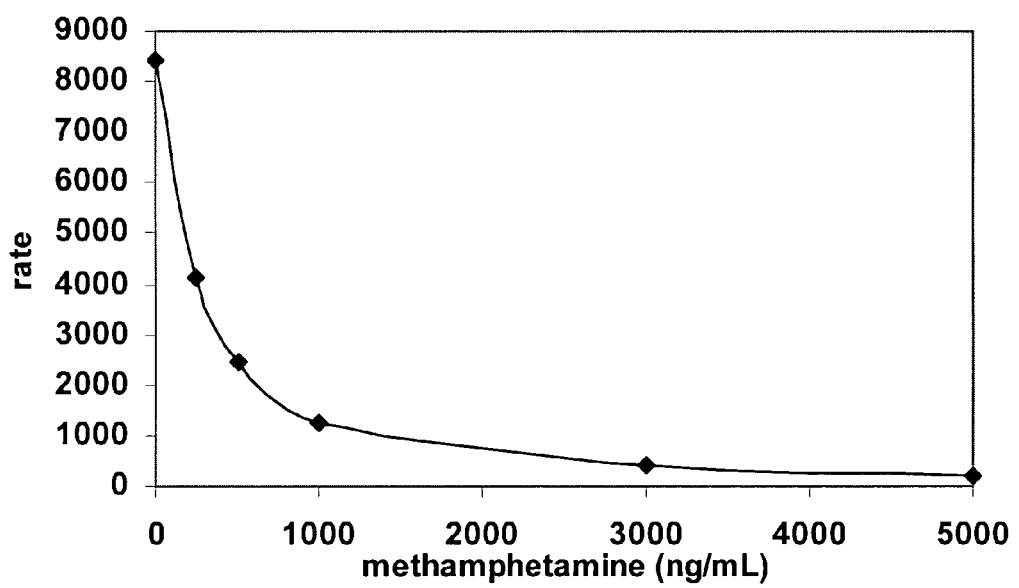
FIG. 11 is a dose response curve generated using the aminodextran conjugate (12) of the present invention with methamphetamine antibody-coated particles.

Percent cross-reactivity was determined in an immunoassay. A standard curve can was established using known amounts of the target analyte methamphetamine. Known amounts of various amphetamine-related drugs were be analyzed as samples in the immunoassay, and apparent concentrations of these drugs were generated from the standard curve. Apparent concentration of the drug, divided by actual concentration and multiplied by 100, is the percent cross-reactivity of this drug. The standard (dose response) curve thus generated is shown in FIG. 11.

The cross-reactivity of the methamphetamine-coated particle with conjugate (12) is given in the table below.

| Compound | Conc (ng/ml) tested | Result | % Cross-reactivity |
| --- | --- | --- | --- |
| d-pseudoephedrine | 100,000 | 326 | 0.3 |
| l-ephedrine | 100,000 | 197 | 0.2 |
| Tyramine | 100,000 | 169 | 0.2 |
| Phentermine | 100,000 | 113 | 0.1 |
| BDB | 2,000 | 69 | 3 |
| MBDB | 1,000 | 467 | 47 |
| MDA | 600 | 38 | 6 |
| d-Amphetamine | 800 | 36 | 5 |
| l-Methamphetamine | 8,000 | 798 | 10 |
| MDEA | 1,000 | 144 | 14 |
| MDMA | 900 | 526 | 58 |
| PPA | 100,000 | 59 | 0.1 |
| Phendimetrazine | 100,000 | 913 | 0.9 |

These results show good cross-reactivity not only to d-methamphetamine but also to ecstasy-class compounds such as MDMA and MBDB. Cross-reactivity with common interfering compounds such as ephedrine, pseudoephedrine, phentermine, and tyramine was minimal, i.e., less than 1%.

EXAMPLE 17

Assay Using Conjugate of Present Invention with N-ethylamphetamine Antibody

The conjugate reagent was prepared as described in Example 16.

An antibody-coated microparticle was prepared as described in Example 16 using monoclonal antibody NEAMP 48.2 described in U.S. patent application Ser. No. 2004/0077021. A microparticle reagent was then prepared as described in Example 16.

The assay was carried out on a Roche/Hitachi 917 analyzer as described in Example 16.

Figure 12:
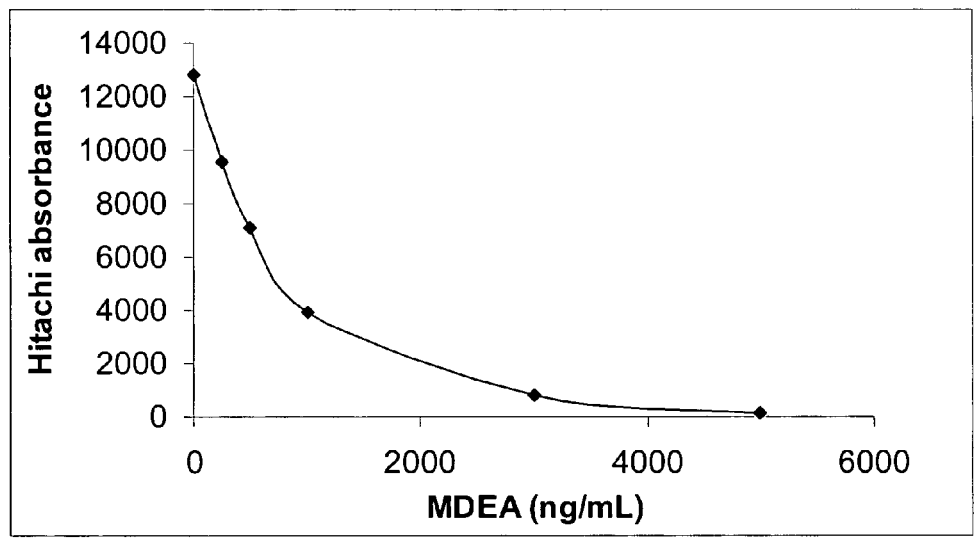
FIG. 12 is a dose response curve generated using the aminodextran conjugate (12) of the present invention with N-ethylamphetamine antibody-coated particles.

Percent cross-reactivity was determined in an immunoassay. A standard curve was established using known amounts of the target analyte methylenedioxyethylamphetamine (MDEA). Known amounts of various amphetamine-related drugs were be analyzed as samples in the immunoassay, and apparent concentrations of these drugs were generated from the standard curve. Apparent concentration of the drug, divided by actual concentration and multiplied by 100, is the percent cross-reactivity of this drug. The standard (dose response) curve thus generated is shown in FIG. 12.

The cross-reactivity of the antibody-coated particle with conjugate (12) is given in the table below.

| Compound | Conc (ng/ml) tested | Result | % Cross-reactivity |
| --- | --- | --- | --- |
| d-Amphetamine | 5000 | 0 | 0.0 |
| d-Methamphetamine | 1000 | 89 | 8.9 |
| l-Methamphetmine | 12500 | 68 | 0.5 |
| MDMA | 1000 | 46 | 4.6 |
| MDA | 5000 | 37 | 0.7 |
| MBDB | 1000 | 59 | 5.9 |
| BDB | 5000 | 47 | 0.9 |
| PPA | 200000 | 70 | 0.04 |
| l-ephedrine | 200000 | 91 | 0.05 |
| d-pseudoephedrine | 200000 | 113 | 0.06 |
| Phentermine | 200000 | 103 | 0.05 |
| Phendimetrazine | 100000 | 44 | 0.04 |
| Tyramine | 200000 | 67 | 0.03 |

These results show good cross-reactivity not only to methylenedioxyethylamphetamine but also cross-reactivity to d-methamphetamine and to ecstasy-class compounds such as MDMA and MBDB. At the same time, cross-reactivity with common interfering compounds such as ephedrine, pseudoephedrine, phentermine, and tyramine was essentially none.

What is claimed is:

1. A compound having the formula

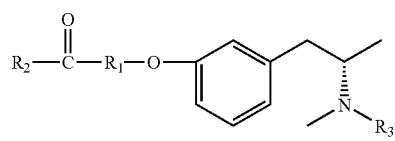

wherein $R_1$ is an alkyl linker comprising 2-15 carbon atoms and 0-6 heteroatoms, $R_2$ is a leaving group, and $R_3$ is a protecting group.

2. The compound of claim 1 wherein $R_3$ is trifluoroacetyl.

3. A compound having the formula

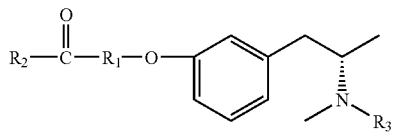

wherein $R_1$ is an alkyl linker comprising 2-15 carbon atoms and 0-6 heteroatoms, $R_2$ is aminodextran, and $R_3$ is a protecting group.

4. The compound of claim 3

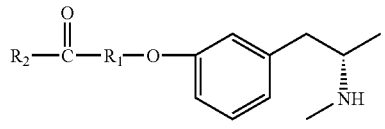

wherein $R_3$ is cleaved and the compound is deprotected.

5. The compound 4-{[4-(3-{(S)-2[methyl-(2,2,2trifluoro-acetyl)-amino]-propyl}-phenoxy)-butyrylamino]-methyl}-benzoicacid 2,5-dioxo-pyrrolidin-1-yl ester having the formula

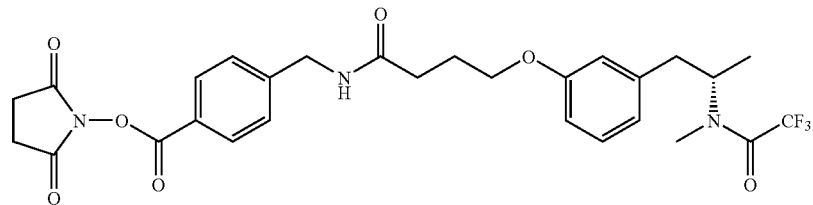

6. The compound having the formula

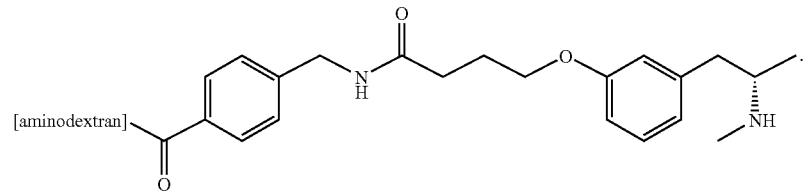

* * * * *